US008431377B2

(12) United States Patent
Fatland-Bloom et al.

(10) Patent No.: US 8,431,377 B2
(45) Date of Patent: Apr. 30, 2013

(54) METHODS OF PRODUCING C4 DICARBOXYLIC ACIDS

(75) Inventors: Beth Fatland-Bloom, Forsyth, IL (US); John P. Rayapati, Monticello, IL (US)

(73) Assignee: Archer Daniels Midland Company, Decatur, IL (US)

( * ) Notice: Subject to any disclaimer, the term of this patent is extended or adjusted under 35 U.S.C. 154(b) by 0 days.

(21) Appl. No.: 13/256,537

(22) PCT Filed: Mar. 23, 2010

(86) PCT No.: PCT/US2010/028211
§ 371 (c)(1),
(2), (4) Date: Sep. 14, 2011

(87) PCT Pub. No.: WO2010/111206
PCT Pub. Date: Sep. 30, 2010

(65) Prior Publication Data
US 2012/0003708 A1    Jan. 5, 2012

Related U.S. Application Data

(60) Provisional application No. 61/162,458, filed on Mar. 23, 2009.

(51) Int. Cl.
*C12N 9/10* (2006.01)
*C12N 15/00* (2006.01)
*C12N 1/20* (2006.01)
*C07H 21/04* (2006.01)

(52) U.S. Cl.
USPC .............. 435/193; 435/252.3; 435/320.1; 536/23.2

(58) Field of Classification Search .......... 435/193, 435/252.3, 320.1; 536/23.2
See application file for complete search history.

(56) References Cited

U.S. PATENT DOCUMENTS

| 6,171,833 | B1 | 1/2001 | Sinskey et al. |
| 6,403,351 | B1 | 6/2002 | Sinskey et al. |
| 6,884,606 | B2 | 4/2005 | Sinskey et al. |
| 6,965,021 | B2 | 11/2005 | Hanke et al. |
| 7,300,777 | B2 | 11/2007 | Hanke et al. |
| 7,566,563 | B2 | 7/2009 | Fatland-Bloom et al. |
| 7,838,278 | B2 * | 11/2010 | Fatland-Bloom et al. . 435/252.3 |

OTHER PUBLICATIONS

Brummelkamp et al., A system for Stable Expression of Short Interfering RNAs in Mammalian Cells, Science, Apr. 19, 2002, vol. 296, pp. 550-553, www.sciencemag.org, USA.
Caplen et al., Specific inhibition of gene expression by small double-stranded RNAs in invertebrate and vertebrate systems, Aug. 14, 2001, vol. 98 No. 17, pp. 9742-9747, www.pnas.org/cgl/dol/10.1073/pnas.171251798, USA.
Broun et al., Catalytic Plasticity of Fatty Acid Modification Enzymes Underlying Chemical Diversity of Plant Lipids, Science, Nov. 13, 1998, vol. 282, pp. 1315-1317, www.sciencemag.org, USA.
Stucka et al., DNA sequences in chromosomes II and VII code for pyruvate carboxylase isoenzymes in Saccharomyces cercisiae: analysis of pyruvate carboxylase-deficient strains, Molecular Genetics & Genomics (1991) 229:307-315.
Engel et al., Fumaric acid production by fermentation, Applied Microbiology and Biotechnoloy (2008) 78:379-389, USA.
Potera et al., Making Succinate More Successful, Environmental Health Perspectives, vol. 113 No. 12, Dec. 2005, A832-A835.
Persengiev et al., Nonspecific, concentration-dependent stimulation and repression of mammalian gene expression by small interfering RNAs (siRNAs), RNA Journal (2004), vol. 10 No. 1, pp. 12-18, USA.
McKinlay et al., Prospects for a bio-based succinate industry, Applied Microbiology and Biotechnology (2007) 76:727-740, USA.
Goldberg et al., Review: Organic acids: old metabolites, new themes, Journal of Chemical Technology and Biotechnology (2006), pp. 1601-1611, USA.
PCT, Written Opinion of the International Searching Authority, Jul. 9, 2010, US Receiving Office.
PCT, International Search Report, Jul. 9, 2010, US Receiving Office.
Devos et al., Practical limits of function prediction. Proteins: Structure, Function, and Genetics, 2000, vol. 41:98-107, USA.
Seffernick et al., Melamine deaminase and Atrazine chlorohydrolase: 98 percent identical but functionally different, J. Bacteriol, 2001, vol. 183 (8): pp. 2405-2410.
Whisstock et al., Prediction of protein function from protein sequence, Q. Rev. Biophysics, 2003, vol. 36 (3): pp. 307-340.
Witkowski et al., Conversion of b-ketoacyl synthase to a Malonyl Decarboxylase by replacement of the active cysteine with glutamine, Biochemistry, 1999, vol. 038: pp. 11643-11650.

\* cited by examiner

*Primary Examiner* — Maryam Monshipouri
(74) *Attorney, Agent, or Firm* — Andrew F. Nilles

(57) ABSTRACT

Methods of producing C4 dicarboxylic acids are disclosed. Nucleotide sequences encoding pyruvate carboxylase and uses of such nucleotide sequences in the production of C4 dicarboxylic acids are further disclosed.

19 Claims, 8 Drawing Sheets

FIG. 3A pyruvate carboxylase cDNA from *Rhizopus oryzae* NRRL 1526

ATGCCTGCTGCACCAGTACGTGAACACTCTGTGGATACCATTCGTAGAAATAGCGAAGTGAT
GGGTAACCTGAGAAAATTGATGGTGGTTAATCGTGGTGAAATTGCTATCCGTGTCTTTCGTA
CAGCTCATGAACTCTCTATGAAGACAGTAGCTATTTTCTCTCATGAAGATAGATTATCCATGC
ACAGATATAAGGCGGATGAATCCTATCAACTCGGTCGTATTGGTCAATACACACCTGTAGGT
GCTTATCTGGCACAAGATGAAGTCGTTCGAATCGCAAAGGAACGTGGTGTGAGCATGATTCA
TCCTGGTTATGGTTTCTTGTCTGAAAATGCTGAATTCGCTCGCAAGGTGGAAGCTGCAGGAA
TCACTTTCATTGGTCCCTCTCCTGATGTCATTGAAAGTTTAGGCGATAAGACAAAAGCCAGA
ACGATTGCCATGAAGTGTGAAGTCCCTGTTGTCCCTGGTACACCTGGACCTGTCAGTGAATA
CAAAGAGGCCCTGAACTTTATCAAAGAATATGGTTTTCCTATCATCATCAAGGCTGCCATGG
GTGGTGGTGGTCGTGGTATGCGTGTGGTTCGTGACGAAGCCAGTCTAGAGGACGCGTTTACC
CGTGCGAAATCTGAAGCTTTGGCTGCCTTTGGTGATGGCACTGTCTTTATCGAACGTTTCCTT
GATAAGCCTCGTCATATCGAGGTTCAATTGTTGGCAGATCGTGCAGGTAACGTGGTCCATCT
CTTTGAACGTGATTGTTCTGTTCAGCGTCGTCACCAAAAGGTGGTTGAAATCGCCCCTGCCA
AAAACTTGGATAACAAGGTACGTGAGGCCATCTTGAACGATGCGATCAAGATTGCCAAGGC
TGTAAAGTACAAGAACGCGGGTACTGCAGAATTCTTGGTGGATAACCAAAACCGTCACTACT
TTATCGAAATCAATCCTCGTATCCAAGTCGAACATACCATCACAGAAGAAATCACGGGTATT
GATATCGTTGCCGCTCAAATTCAGATCGCTGCCGGTGCCCTCTTGCCTCAATTGGGTCTTACC
CAACAACGTATCCGTCAACGTGGGTTCGCGATCCAGTGTCGTGTGACAACCGAGGACCCCGA
AAAGAATTTCCAGCCTGACACGGGTAAGATCGAAGTGTACCGTTCCTCTGGTGGTAACGGTG
TTCGTCTGGATGGTGGTGCTGGTTACGCAGGTGCTATCATTACCCCTCACTATGATTCACTTT
TGGTCAAAGTCTCTTGTTCTGGATCCACCTACGAAGTCGCTCGTCGCAAGATCGTCCGTGCCT
TGGTCGAATTCAGAATCCGTGGTGTCAAGACCAATATCCCCTTCTTACAACGTCTCTTGACCC
ATGATACCTTCATCAACGGTAACTGCTGGACAACTTTCATTGATGATACTCCCGATCTTTTCC
GTCTTGTTCAATTCCAAAACCGTGCTCAAAGACTCTTGGGTTACCTGGGTGATGTCGTCGTCA
ATGGTTCTCAAATCAAGGGTCAAATGGGTGATCCCATTCTGAAGCAAGAGATCGAAATCCCC
GTGTTGCGTGAAAGTGGTAGTGACAAGACGGTCGATGTCTCTGCTCCTGCTACGGAAGGCTG
GAGAAAGATCATTGTGGAACAAGGACCTGAAGCTTTCGCAAAAGCTGTCCGTGCTTACCCTG
GTGTCTTGATCACCGATACCACCTGGAGAGACGCTCATCAGAGTTTATTGGCCACTCGTGTG
AGAACTGTCGATCTCTTGCGTATCGCCCCTGCTACCTCTCACGCTTTGGCCAACGCCTTTTCA
TTGGAATGTTGGGGAGGTGCTACGTTTGATGTTGCTATGCGTTTCCTTCATGAAGATCCTTGG

FIG. 3B

GACCGTCTTGCTGCTTTGCGAAAGTTGGTACCCAATGTACCCTTCCAAATGCTTTTGCGTGGT
GCCAATGCGGTAGGTTACACCTCTTACCCTGATAACGTTATCTATGAATTCTGTGACAAGGC
AGTCAAGTGTGGTATGGATGTCTTCCGTATCTTTGACTCTCTCAATTATGTTGAAAACATGAG
ATTGGGTATTGACGCTGTCAAGAAGGCCGGTGGTGTTGTTGAAGCCACCATCTGTTACACGG
GTGATGTCTCCAACCCTAACCGCAAGAAGTACGACTTGAAGTACTACCTTGACCTGACACAA
TCCTTGGTGAACGAAGGTATTCACATCTTGGGTATCAAGGACATGGCTGGTCTTCTCAAACC
CGAGGCAGCCAAGTTACTGGTCTCCAGTATCCGTGCCAAGTTCCCCGACTTGCCCATTCACG
TTCACACACACGATACCGCAGGTACGGGTGTTGCTAGCATGATGGCCGCTGCCGCTGCTGGT
GCTGACATTGTTGATGTTGCCGTGGACGCCATGTCCGGCATGACCTCTCAACCGGCGATGGG
TGCCATTGTCGCTGGACTTGAACAGACCAATTTGGGTACCGGTATCCGCATGGAAGACATTC
ATGCCATCAATTCTTACTGGGAGCAATGCCGTTTGCTTTACTCTTGCTTCGAAGCCAACGTGC
GTTCGGCCGATTCGGGTGTCTATGAACATGAAATGCCTGGTGGACAATATACCAACTTGATG
TTCCAAGCCCAACAACTCGGCTTGGGAACTCAGTGGAAGCAAATCAAGAAGGCTTACAAGG
AGGCCAACGAACTCTGTGGTGACTTGGTCAAGGTCACGCCTTCGTCCAAGGTCGTGGGTGAT
CTTGCTCAATTCATGGTTTCCAACCAACTCTCTGCCAAAGAATTTGAAGAACGCGCCTCGAG
TCTCTCTCTGCCCACCTCTGTCATCGAGTTCTTCCAAGGTTATCTCGGTCAACCCTATGGCGG
TTTCCCCGAGCCCTTGCGCTCCAACATCCTTCGTGATCTCCCTCGCCTCGACGGTCGCCCTGG
TGCTAGCCTGCCTCCGTTGGACATGGCTAAACTCAAGGAAGAGTTGGTTGAAAAGTACGGTT
CGAGCATCCGTGATTACGACGTGATCTCGGCTGCTCTTTACCCCAAGGTCTTTGCCGACTACC
GTGATACCGTCAGTCAATACGGTGATCTCTCCGTTTTGCCTACACGCTACTTTTTGTCCAAGC
CCGAGATCAATGAAGAATTCCATGTGGAGATTGAAGAAGGAAAGACGTTGATCATCAAGTT
ATTGGCCGTCGGTCCTCTGAACAATGACGGTAAACGTGATGTTTACTTTGAATTGAACGGTG
AAGCTCGTGTGGTGGGCATTGTGGATCGCAATTCTGCTATTGAAATCGTCACACGTGAAAAG
GCCAACCCCTCCAACCCCGGTGACATTGGTGCTCCTATGTCGGGTGTGGTTGTCGAGATCCG
TGCCAAGGAAGGTAGCCATGTCAAGGCCAGTGATCCTCTGGCTGTTCTCTCTGCTATGAAGA
TGGAAACAGTGGTCACTGCTCCCGTGGCTGGTAGAGTTGAGCGTGTTGCTATCCAAGAAGGT
GATTCATTATCCGCTGGTGATTTGGTGGCCAAGGTTGTCAAAGAGGAAGCCTAA (SEQ ID NO: 1)

FIG. 3C pyruvate carboxylase protein translated from pyrC cDNA from *R. oryzae* 1526

MPAAPVREHSVDTIRRNSEVMGNLRKLMVVNRGEIAIRVFRTAHELSMKTVAIFSHEDRLSMHR
YKADESYQLGRIGQYTPVGAYLAQDEVVRIAKERGVSMIHPGYGFLSENAEFARKVEAAGITFIG
PSPDVIESLGDKTKARTIAMKCEVPVVPGTPGPVSEYKEALNFIKEYGFPIIIKAAMGGGGRGMRV
VRDEASLEDAFTRAKSEALAAFGDGTVFIERFLDKPRHIEVQLLADRAGNVVHLFERDCSVQRR
HQKVVEIAPAKNLDNKVREAILNDAIKIAKAVKYKNAGTAEFLVDNQNRHYFIEINPRIQVEHTIT
EEITGIDIVAAQIQIAAGALLPQLGLTQQRIRQRGFAIQCRVTTEDPEKNFQPDTGKIEVYRSSGGN
GVRLDGGAGYAGAIITPHYDSLLVKVSCSGSTYEVARRKIVRALVEFRIRGVKTNIPFLQRLLTHD
TFINGNCWTTFIDDTPDLFRLVQFQNRAQRLLGYLGDVVVNGSQIKGQMGDPILKQEIEIPVLRES
GSDKTVDVSAPATEGWRKIIVEQGPEAFAKAVRAYPGVLITDTTWRDAHQSLLATRVRTVDLLR
IAPATSHALANAFSLECWGGATFDVAMRFLHEDPWDRLAALRKLVPNVPFQMLLRGANAVGYT
SYPDNVIYEFCDKAVKCGMDVFRIFDSLNYVENMRLGIDAVKKAGGVVEATICYTGDVSNPNR
KKYDLKYYLDLTQSLVNEGIHILGIKDMAGLLKPEAAKLLVSSIRAKFPDLPIHVHTHDTAGTGV
ASMMAAAAAGADIVDVAVDAMSGMTSQPAMGAIVAGLEQTNLGTGIRMEDIHAINSYWEQCR
LLYSCFEANVRSADSGVYEHEMPGGQYTNLMFQAQQLGLGTQWKQIKKAYKEANELCGDLVK
VTPSSKVVGDLAQFMVSNQLSAKEFEERASSLSLPTSVIEFFQGYLGQPYGGFPEPLRSNILRDLP
RLDGRPGASLPPLDMAKLKEELVEKYGSSIRDYDVISAALYPKVFADYRDTVSQYGDLSVLPTR
YFLSKPEINEEFHVEIEEGKTLIIKLLAVGPLNNDGKRDVYFELNGEARVVGIVDRNSAIEIVTREK
ANPSNPGDIGAPMSGVVVEIRAKEGSHVKASDPLAVLSAMKMETVVTAPVAGRVERVAIQEGD
SLSAGDLVAKVVKEEA (SEQ ID NO: 2)

SEQUENCE LISTING

<160> NUMBER OF SEQ ID NOS: 19

<210> SEQ ID NO 1
<211> LENGTH: 3540
<212> TYPE: DNA

-continued

<213> ORGANISM: Rhizopus oryzae

<400> SEQUENCE: 1

| | | | | | |
|---|---|---|---|---|---|
| atgcctgctg | caccagtacg | tgaacactct | gtggatacca | ttcgtagaaa | tagcgaagtg | 60 |
| atgggtaacc | tgagaaaatt | gatggtggtt | aatcgtggtg | aaattgctat | ccgtgtcttt | 120 |
| cgtacagctc | atgaactctc | tatgaagaca | gtagctattt | tctctcatga | agatagatta | 180 |
| tccatgcaca | gatataaggc | ggatgaatcc | tatcaactcg | gtcgtattgg | tcaatacaca | 240 |
| cctgtaggtg | cttatctggc | acaagatgaa | gtcgttcgaa | tcgcaaagga | acgtggtgtg | 300 |
| agcatgattc | atcctggtta | tggtttcttg | tctgaaaatg | ctgaattcgc | tcgcaaggtg | 360 |
| gaagctgcag | gaatcacttt | cattggtccc | tctcctgatg | tcattgaaag | tttaggcgat | 420 |
| aagacaaaag | ccagaacgat | tgccatgaag | tgtgaagtcc | ctgttgtccc | tggtacacct | 480 |
| ggacctgtca | gtgaatacaa | agaggccctg | aactttatca | agaatatgg | ttttcctatc | 540 |
| atcatcaagg | ctgccatggg | tggtggtggt | cgtggtatgc | gtgtggttcg | tgacgaagcc | 600 |
| agtctagagg | acgcgtttac | ccgtgcgaaa | tctgaagctt | tggctgcctt | tggtgatggc | 660 |
| actgtcttta | tcgaacgttt | ccttgataag | cctcgtcata | tcgaggttca | attgttggca | 720 |
| gatcgtgcag | gtaacgtggt | ccatctcttt | gaacgtgatt | gttctgttca | gcgtcgtcac | 780 |
| caaaaggtgg | ttgaaatcgc | ccctgccaaa | aacttggata | caaggtacg | tgaggccatc | 840 |
| ttgaacgatg | cgatcaagat | tgccaaggct | gtaaagtaca | gaacgcggg | tactgcagaa | 900 |
| ttcttggtgg | ataaccaaaa | ccgtcactac | tttatcgaaa | tcaatcctcg | tatccaagtc | 960 |
| gaacatacca | tcacagaaga | aatcacgggt | attgatatcg | ttgccgctca | aattcagatc | 1020 |
| gctgccggtg | ccctcttgcc | tcaattgggt | cttacccaac | aacgtatccg | tcaacgtggg | 1080 |
| ttcgcgatcc | agtgtcgtgt | gacaaccgag | gaccccgaaa | agaatttcca | gcctgacacg | 1140 |
| ggtaagatcg | aagtgtaccg | ttcctctggt | ggtaacggtg | ttcgtctgga | tggtggtgct | 1200 |
| ggttacgcag | gtgctatcat | taccccctcac | tatgattcac | ttttggtcaa | agtctcttgt | 1260 |
| tctggatcca | cctacgaagt | cgctcgtcgc | aagatcgtcc | gtgccttggt | cgaattcaga | 1320 |
| atccgtggtg | tcaagaccaa | tatccccttc | ttacaacgtc | tcttgaccca | tgataccttc | 1380 |
| atcaacggta | actgctggac | aactttcatt | gatgatactc | ccgatctttt | ccgtcttgtt | 1440 |
| caattccaaa | accgtgctca | agactcttg | ggttacctgg | gtgatgtcgt | cgtcaatggt | 1500 |
| tctcaaatca | gggtcaaat | gggtgatccc | attctgaagc | aagagatcga | atccccgtg | 1560 |
| ttgcgtgaaa | gtggtagtga | caagacggtc | gatgtctctg | ctcctgctac | ggaaggctgg | 1620 |
| agaaagatca | ttgtggaaca | aggacctgaa | gctttcgcaa | agctgtccg | tgcttaccct | 1680 |
| ggtgtcttga | tcaccgatac | cacctggaga | gacgctcatc | agagtttatt | ggccactcgt | 1740 |
| gtgagaactg | tcgatctctt | gcgtatcgcc | cctgctacct | ctcacgcttt | ggccaacgcc | 1800 |
| ttttcattgg | aatgttgggg | aggtgctacg | tttgatgttg | ctatgcgttt | ccttcatgaa | 1860 |
| gatccttggg | accgtcttgc | tgctttgcga | aagttggtac | ccaatgtacc | cttccaaatg | 1920 |
| cttttgcgtg | gtgccaatgc | ggtaggttac | acctcttacc | ctgataacgt | tatctatgaa | 1980 |
| ttctgtgaca | aggcagtcaa | gtgtggtatg | gatgtcttcc | gtatctttga | ctctctcaat | 2040 |
| tatgttgaaa | acatgagatt | gggtattgac | gctgtcaaga | aggccggtgg | tgttgttgaa | 2100 |
| gccaccatct | gttacacggg | tgatgtctcc | aaccctaacc | gcaagaagta | cgacttgaag | 2160 |
| tactaccttg | acctgacaca | atccttggtg | aacgaaggta | ttcacatctt | gggtatcaag | 2220 |
| gacatggctg | gtcttctcaa | acccgaggca | gccaagttac | tggtctccag | tatccgtgcc | 2280 |

```
aagttccccg acttgcccat tcacgttcac acacacgata ccgcaggtac gggtgttgct    2340
agcatgatgg ccgctgccgc tgctggtgct gacattgttg atgttgccgt ggacgccatg    2400
tccggcatga cctctcaacc ggcgatgggt gccattgtcg ctggacttga acagaccaat    2460
ttgggtaccg gtatccgcat ggaagacatt catgccatca attcttactg ggagcaatgc    2520
cgtttgcttt actcttgctt cgaagccaac gtgcgttcgg ccgattcggg tgtctatgaa    2580
catgaaatgc ctggtggaca atataccaac ttgatgttcc aagcccaaca actcggcttg    2640
ggaactcagt ggaagcaaat caagaaggct tacaaggagg ccaacgaact ctgtggtgac    2700
ttggtcaagg tcacgccttc gtccaaggtc gtgggtgatc ttgctcaatt catggtttcc    2760
aaccaactct ctgccaaaga atttgaagaa cgcgcctcga gtctctctct gcccacctct    2820
gtcatcgagt tcttccaagg ttatctcggt caacccatg gcggtttccc cgagcccttg     2880
cgctccaaca tccttcgtga tctccctcgc ctcgacggtc gccctggtgc tagcctgcct    2940
ccgttggaca tggctaaact caaggaagag ttggttgaaa agtacggttc gagcatccgt    3000
gattacgacg tgatctcggc tgctctttac cccaaggtct ttgccgacta ccgtgatacc    3060
gtcagtcaat acggtgatct ctccgttttg cctacacgct acttttgtc caagcccgag     3120
atcaatgaag aattccatgt ggagattgaa gaaggaaaga cgttgatcat caagttattg    3180
gccgtcggtc ctctgaacaa tgacggtaaa cgtgatgttt actttgaatt gaacggtgaa    3240
gctcgtgtgg tgggcattgt ggatcgcaat tctgctattg aaatcgtcac acgtgaaaag    3300
gccaacccct ccaaccccgg tgacattggt gctcctatgt cgggtgtggt tgtcgagatc    3360
cgtgccaagg aaggtagcca tgtcaaggcc agtgatcctc tggctgttct ctctgctatg    3420
aagatggaaa cagtggtcac tgctcccgtg gctggtagag ttgagcgtgt tgctatccaa    3480
gaaggtgatt cattatccgc tggtgatttg gtggccaagg ttgtcaaaga ggaagcctaa    3540
```

<210> SEQ ID NO 2
<211> LENGTH: 1179
<212> TYPE: PRT
<213> ORGANISM: Rhizopus oryzae

<400> SEQUENCE: 2

```
Met Pro Ala Ala Pro Val Arg Glu His Ser Val Asp Thr Ile Arg Arg
1               5                   10                  15

Asn Ser Glu Val Met Gly Asn Leu Arg Lys Leu Met Val Val Asn Arg
                20                  25                  30

Gly Glu Ile Ala Ile Arg Val Phe Arg Thr Ala His Glu Leu Ser Met
            35                  40                  45

Lys Thr Val Ala Ile Phe Ser His Glu Asp Arg Leu Ser Met His Arg
        50                  55                  60

Tyr Lys Ala Asp Glu Ser Tyr Gln Leu Gly Arg Ile Gly Gln Tyr Thr
65                  70                  75                  80

Pro Val Gly Ala Tyr Leu Ala Gln Asp Glu Val Arg Ile Ala Lys
                85                  90                  95

Glu Arg Gly Val Ser Met Ile His Pro Gly Tyr Gly Phe Leu Ser Glu
            100                 105                 110

Asn Ala Glu Phe Ala Arg Lys Val Glu Ala Ala Gly Ile Thr Phe Ile
        115                 120                 125

Gly Pro Ser Pro Asp Val Ile Glu Ser Leu Gly Asp Lys Thr Lys Ala
    130                 135                 140

Arg Thr Ile Ala Met Lys Cys Glu Val Pro Val Pro Gly Thr Pro
145                 150                 155                 160
```

```
Gly Pro Val Ser Glu Tyr Lys Glu Ala Leu Asn Phe Ile Lys Glu Tyr
                165                 170                 175
Gly Phe Pro Ile Ile Lys Ala Ala Met Gly Gly Gly Arg Gly
            180                 185                 190
Met Arg Val Val Arg Asp Glu Ala Ser Leu Glu Asp Ala Phe Thr Arg
            195                 200                 205
Ala Lys Ser Glu Ala Leu Ala Ala Phe Gly Asp Gly Thr Val Phe Ile
        210                 215                 220
Glu Arg Phe Leu Asp Lys Pro Arg His Ile Glu Val Gln Leu Leu Ala
225                 230                 235                 240
Asp Arg Ala Gly Asn Val Val His Leu Phe Glu Arg Asp Cys Ser Val
                245                 250                 255
Gln Arg Arg His Gln Lys Val Val Glu Ile Ala Pro Ala Lys Asn Leu
            260                 265                 270
Asp Asn Lys Val Arg Glu Ala Ile Leu Asn Asp Ala Ile Lys Ile Ala
        275                 280                 285
Lys Ala Val Lys Tyr Lys Asn Ala Gly Thr Ala Glu Phe Leu Val Asp
        290                 295                 300
Asn Gln Asn Arg His Tyr Phe Ile Glu Ile Asn Pro Arg Ile Gln Val
305                 310                 315                 320
Glu His Thr Ile Thr Glu Ile Thr Gly Ile Asp Ile Val Ala Ala
                325                 330                 335
Gln Ile Gln Ile Ala Ala Gly Ala Leu Leu Pro Gln Leu Gly Leu Thr
            340                 345                 350
Gln Gln Arg Ile Arg Gln Arg Gly Phe Ala Ile Gln Cys Arg Val Thr
            355                 360                 365
Thr Glu Asp Pro Glu Lys Asn Phe Gln Pro Asp Thr Gly Lys Ile Glu
        370                 375                 380
Val Tyr Arg Ser Ser Gly Gly Asn Gly Val Arg Leu Asp Gly Gly Ala
385                 390                 395                 400
Gly Tyr Ala Gly Ala Ile Ile Thr Pro His Tyr Asp Ser Leu Leu Val
                405                 410                 415
Lys Val Ser Cys Ser Gly Ser Thr Tyr Glu Val Ala Arg Arg Lys Ile
            420                 425                 430
Val Arg Ala Leu Val Glu Phe Arg Ile Arg Gly Val Lys Thr Asn Ile
            435                 440                 445
Pro Phe Leu Gln Arg Leu Leu Thr His Asp Thr Phe Ile Asn Gly Asn
        450                 455                 460
Cys Trp Thr Thr Phe Ile Asp Asp Thr Pro Asp Leu Phe Arg Leu Val
465                 470                 475                 480
Gln Phe Gln Asn Arg Ala Gln Arg Leu Leu Gly Tyr Leu Gly Asp Val
                485                 490                 495
Val Val Asn Gly Ser Gln Ile Lys Gly Gln Met Gly Asp Pro Ile Leu
            500                 505                 510
Lys Gln Glu Ile Glu Ile Pro Val Leu Arg Glu Ser Gly Ser Asp Lys
            515                 520                 525
Thr Val Asp Val Ser Ala Pro Thr Glu Gly Trp Arg Lys Ile Ile
        530                 535                 540
Val Glu Gln Gly Pro Glu Ala Phe Ala Lys Ala Val Arg Ala Tyr Pro
545                 550                 555                 560
Gly Val Leu Ile Thr Asp Thr Thr Trp Arg Asp Ala His Gln Ser Leu
                565                 570                 575
Leu Ala Thr Arg Val Arg Thr Val Asp Leu Leu Arg Ile Ala Pro Ala
            580                 585                 590
```

```
Thr Ser His Ala Leu Ala Asn Ala Phe Ser Leu Glu Cys Trp Gly Gly
        595                 600                 605

Ala Thr Phe Asp Val Ala Met Arg Phe Leu His Glu Asp Pro Trp Asp
        610                 615                 620

Arg Leu Ala Ala Leu Arg Lys Leu Val Pro Asn Val Pro Phe Gln Met
625                 630                 635                 640

Leu Leu Arg Gly Ala Asn Ala Val Gly Tyr Thr Ser Tyr Pro Asp Asn
                645                 650                 655

Val Ile Tyr Glu Phe Cys Asp Lys Ala Val Lys Cys Gly Met Asp Val
        660                 665                 670

Phe Arg Ile Phe Asp Ser Leu Asn Tyr Val Glu Asn Met Arg Leu Gly
        675                 680                 685

Ile Asp Ala Val Lys Lys Ala Gly Val Val Glu Ala Thr Ile Cys
        690                 695                 700

Tyr Thr Gly Asp Val Ser Asn Pro Asn Arg Lys Lys Tyr Asp Leu Lys
705                 710                 715                 720

Tyr Tyr Leu Asp Leu Thr Gln Ser Leu Val Asn Glu Gly Ile His Ile
                725                 730                 735

Leu Gly Ile Lys Asp Met Ala Gly Leu Leu Lys Pro Glu Ala Ala Lys
        740                 745                 750

Leu Leu Val Ser Ser Ile Arg Ala Lys Phe Pro Asp Leu Pro Ile His
        755                 760                 765

Val His Thr His Asp Thr Ala Gly Thr Gly Val Ala Ser Met Met Ala
770                 775                 780

Ala Ala Ala Ala Gly Ala Asp Ile Val Asp Val Ala Val Asp Ala Met
785                 790                 795                 800

Ser Gly Met Thr Ser Gln Pro Ala Met Gly Ala Ile Val Ala Gly Leu
                805                 810                 815

Glu Gln Thr Asn Leu Gly Thr Gly Ile Arg Met Glu Asp Ile His Ala
        820                 825                 830

Ile Asn Ser Tyr Trp Glu Gln Cys Arg Leu Leu Tyr Ser Cys Phe Glu
        835                 840                 845

Ala Asn Val Arg Ser Ala Asp Ser Gly Val Tyr Glu His Glu Met Pro
850                 855                 860

Gly Gly Gln Tyr Thr Asn Leu Met Phe Gln Ala Gln Gln Leu Gly Leu
865                 870                 875                 880

Gly Thr Gln Trp Lys Gln Ile Lys Lys Ala Tyr Lys Glu Ala Asn Glu
                885                 890                 895

Leu Cys Gly Asp Leu Val Lys Val Thr Pro Ser Ser Lys Val Val Gly
        900                 905                 910

Asp Leu Ala Gln Phe Met Val Ser Asn Gln Leu Ser Ala Lys Glu Phe
        915                 920                 925

Glu Glu Arg Ala Ser Ser Leu Ser Leu Pro Thr Ser Val Ile Glu Phe
930                 935                 940

Phe Gln Gly Tyr Leu Gly Gln Pro Tyr Gly Gly Phe Pro Glu Pro Leu
945                 950                 955                 960

Arg Ser Asn Ile Leu Arg Asp Leu Pro Arg Leu Asp Gly Arg Pro Gly
                965                 970                 975

Ala Ser Leu Pro Pro Leu Asp Met Ala Lys Leu Lys Glu Glu Leu Val
        980                 985                 990

Glu Lys Tyr Gly Ser Ser Ile Arg Asp Tyr Asp Val Ile Ser Ala Ala
        995                 1000                1005

Leu Tyr Pro Lys Val Phe Ala Asp Tyr Arg Asp Thr Val Ser Gln
```

-continued

```
                    1010                1015                1020

Tyr Gly Asp Leu Ser Val Leu Pro Thr Arg Tyr Phe Leu Ser Lys
    1025                1030                1035

Pro Glu Ile Asn Glu Glu Phe His Val Glu Ile Glu Glu Gly Lys
    1040                1045                1050

Thr Leu Ile Ile Lys Leu Leu Ala Val Gly Pro Leu Asn Asn Asp
    1055                1060                1065

Gly Lys Arg Asp Val Tyr Phe Glu Leu Asn Gly Glu Ala Arg Val
    1070                1075                1080

Val Gly Ile Val Asp Arg Asn Ser Ala Ile Glu Ile Val Thr Arg
    1085                1090                1095

Glu Lys Ala Asn Pro Ser Asn Pro Gly Asp Ile Gly Ala Pro Met
    1100                1105                1110

Ser Gly Val Val Val Glu Ile Arg Ala Lys Glu Gly Ser His Val
    1115                1120                1125

Lys Ala Ser Asp Pro Leu Ala Val Leu Ser Ala Met Lys Met Glu
    1130                1135                1140

Thr Val Val Thr Ala Pro Val Ala Gly Arg Val Glu Arg Val Ala
    1145                1150                1155

Ile Gln Glu Gly Asp Ser Leu Ser Ala Gly Asp Leu Val Ala Lys
    1160                1165                1170

Val Val Lys Glu Glu Ala
    1175

<210> SEQ ID NO 3
<211> LENGTH: 19
<212> TYPE: RNA
<213> ORGANISM: Artificial Sequence
<220> FEATURE:
<223> OTHER INFORMATION: siRNA designed to silence pyruvate
      dehydrogenase sequence from Rhizopus oryzae

<400> SEQUENCE: 3
cagacgauga ccuuccuua                                              19

<210> SEQ ID NO 4
<211> LENGTH: 19
<212> TYPE: RNA
<213> ORGANISM: Artificial Sequence
<220> FEATURE:
<223> OTHER INFORMATION: siRNA designed to silence the pyruvate
      dehydrogenase sequence from Rhizopus oryzae

<400> SEQUENCE: 4
uaaggaaggu caucgucug                                              19

<210> SEQ ID NO 5
<211> LENGTH: 19
<212> TYPE: RNA
<213> ORGANISM: Artificial Sequence
<220> FEATURE:
<223> OTHER INFORMATION: siRNA designed to silence pyruvate
      decarboxylase from Rhizopus oryzae

<400> SEQUENCE: 5
cuuugaugug uucuucaac                                              19

<210> SEQ ID NO 6
<211> LENGTH: 19
<212> TYPE: RNA
<213> ORGANISM: Artificial Sequence
<220> FEATURE:
```

-continued

```
<223> OTHER INFORMATION: siRNA designed to silence pyruate decarboxylase
      from Rhizopus oryzae

<400> SEQUENCE: 6
guugaagaac acaucaaag                                                  19

<210> SEQ ID NO 7
<211> LENGTH: 17
<212> TYPE: RNA
<213> ORGANISM: Artificial Sequence
<220> FEATURE:
<223> OTHER INFORMATION: siRNA designed to silence pyruvate carboxylase
      from Rhizopus oryzae

<400> SEQUENCE: 7
uuggccacuc gugugag                                                    17

<210> SEQ ID NO 8
<211> LENGTH: 17
<212> TYPE: RNA
<213> ORGANISM: Artificial Sequence
<220> FEATURE:
<223> OTHER INFORMATION: siRNA designed to silence pyruvate carboxylase
      from Rhizopus oryzae

<400> SEQUENCE: 8
cucacacgag uggccaa                                                    17

<210> SEQ ID NO 9
<211> LENGTH: 20
<212> TYPE: DNA
<213> ORGANISM: Artificial Sequence
<220> FEATURE:
<223> OTHER INFORMATION: degenerate forward primer based on conserved
      amino acid sequences of pyruvate carboxylase homologs from
      Aspergillus agricarus, Aspergillus terreus, Pichia pastoris and
      Schizosaccharomyces pombe

<400> SEQUENCE: 9
caragragrc aycaraargt                                                 20

<210> SEQ ID NO 10
<211> LENGTH: 20
<212> TYPE: DNA
<213> ORGANISM: Artificial Sequence
<220> FEATURE:
<223> OTHER INFORMATION: degenerate reverse primer based on conserved
      amino acid sequences of pyruvate carboxylase homologs from
      Aspergillus agricarus, Aspergillus terreus, Pichia pastoris and
      Schizosaccharomyces pombe
<220> FEATURE:
<221> NAME/KEY: misc_feature
<222> LOCATION: (12)..(12)
<223> OTHER INFORMATION: n is a, c, g, or t
<220> FEATURE:
<221> NAME/KEY: misc_feature
<222> LOCATION: (15)..(15)
<223> OTHER INFORMATION: n is a, c, g, or t

<400> SEQUENCE: 10
tcrtcdatra angtngtcca                                                 20

<210> SEQ ID NO 11
<211> LENGTH: 7
<212> TYPE: PRT
<213> ORGANISM: Artificial Sequence
<220> FEATURE:
<223> OTHER INFORMATION: convserved amino acid sequence of pyruvate
      carboxylase from Aspergillus agricarus, Aspergillus terreus,
      Pichia pastoris and Schizosaccharomyces pombe
```

```
<400> SEQUENCE: 11

Trp Thr Thr Phe Ile Asp Asp
1               5

<210> SEQ ID NO 12
<211> LENGTH: 28
<212> TYPE: DNA
<213> ORGANISM: Artificial Sequence
<220> FEATURE:
<223> OTHER INFORMATION: pyruvate carboxylase specific oligonucleotide
      used to prime first-strand cDNA synthesis

<400> SEQUENCE: 12
ccaatacgac cgagttgata ggattcat                                        28

<210> SEQ ID NO 13
<211> LENGTH: 23
<212> TYPE: DNA
<213> ORGANISM: Artificial Sequence
<220> FEATURE:
<223> OTHER INFORMATION: nester primer used to amplify first-strand cDNA
      produced from SEQ ID NO: 12

<400> SEQUENCE: 13
gcatagataa tgtatcttca tga                                             23

<210> SEQ ID NO 14
<211> LENGTH: 20
<212> TYPE: DNA
<213> ORGANISM: Artificial Sequence
<220> FEATURE:
<223> OTHER INFORMATION: pyruvate carboxylase specific primer

<400> SEQUENCE: 14
ataacgatgc ctgctgcacc                                                 20

<210> SEQ ID NO 15
<211> LENGTH: 23
<212> TYPE: DNA
<213> ORGANISM: Artificial Sequence
<220> FEATURE:
<223> OTHER INFORMATION: nested oligo dT primer used to amplify pyruvate
      carboxylase

<400> SEQUENCE: 15
cgctacgtaa cggcatgaca gtg                                             23

<210> SEQ ID NO 16
<211> LENGTH: 19
<212> TYPE: DNA
<213> ORGANISM: Artificial Sequence
<220> FEATURE:
<223> OTHER INFORMATION: primer specific for pyrC from Rhizopus oryzae

<400> SEQUENCE: 16
ggacttcaca ctgcatggc                                                  19

<210> SEQ ID NO 17
<211> LENGTH: 22
<212> TYPE: DNA
<213> ORGANISM: Artificial Sequence
<220> FEATURE:
<223> OTHER INFORMATION: primer specific for pyrG from Rhizopus oryzae

<400> SEQUENCE: 17
gcttgtctac caattaggtg ca                                              22
```

```
<210> SEQ ID NO 18
<211> LENGTH: 20
<212> TYPE: DNA
<213> ORGANISM: Artificial Sequence
<220> FEATURE:
<223> OTHER INFORMATION: primer specific for pyrG

<400> SEQUENCE: 18
ccgagccaca gatcaggaat                                               20

<210> SEQ ID NO 19
<211> LENGTH: 29
<212> TYPE: DNA
<213> ORGANISM: Artificial Sequence
<220> FEATURE:
<223> OTHER INFORMATION: primer specific for Ptef:fum junction

<400> SEQUENCE: 19
gcagaagctc gcaacatggc tatgatgaa                                     29
```

US 8,431,377 B2

METHODS OF PRODUCING C4 DICARBOXYLIC ACIDS

CROSS-REFERENCE TO RELATED APPLICATIONS

This application is a national stage entry of International Application No. PCT/US10/028,211, filed Mar. 23, 2010, which itself claims priority to U.S. Provisional Patent Application No. 61/162,458, filed Mar. 23, 2009, each of the contents of the entirety of which are incorporated by this reference.

TECHNICAL FIELD

The present invention relates generally to the production of C4 dicarboxylic acids.

BACKGROUND

Dicarboxylic acids include two carboxylic acid groups and have a number of uses including, but not limited to, food additives, polymer plasticizers, solvents, lubricants, engineered plastics, epoxy curing agents, adhesive and powder coatings, corrosion inhibitors, cosmetics, pharmaceuticals, and electrolytes. Such dicarboxylic acids can also be converted into their ester forms for a different variety of different uses.

Dicarboxylic acids such as malic, fumaric and succinic acids can be produced by chemical synthesis or fermentation. Since the production of dicarboxylic acids by chemical synthesis can result in harmful waste by-products, a need exists for the production of dicarboxylic acids by fermentation.

Malic acid is an organic acid having utility in the food production industry and is used for making cosmetics. Malic acid is also used in the chemical industry as a surfactant or biodegradable polymer. The malic acid can also be subjected to various processes to product hydroxybutyrolactone and hydroxysuccinate derivatives, maleic anhydride and 1,4-butanediol.

Fumaric acid is an organic acid widely found in nature. In humans and other mammals, fumaric acid is a key intermediate in the tricarboxylic acid cycle for organic acid biosynthesis (also known as the Krebs cycle or the citric acid cycle). Fumaric acid is also an essential ingredient in plant life and finds utility in the food industry; as a chemical intermediate in the production of malic acid and aspartic acid; as an industrial chemical in the manufacture of polyester resins or polyhydric alcohols; as a mordant for dyes; or can be used in the production of a wide variety of industrial chemicals.

Succinic acid is an organic acid finding utility as a surfactant, a detergent, an extender or a foaming agent. Succinic acid can also be an ion chelator, used in the food or feed industry, used in the pharmaceutical or health products markets or as a plant stimulant. Like malic acid and fumaric acid, succinic acid can also be used as an industrial chemical such as in the production of adipic acid, 4-amino butanoic acid, aspartic acid, 1,4-butanediol, diethyl succinate, ethylenediaminedisuccinate, fumaric acid, gamma-butyrolactone, hydroxysuccinide, itaconic acid, maleic acid, maleic anhydride, maleimide, malic acid, N-methylpyrrolidone, 2-pyrrolidione, succinimide, tetrahydrofuran or other 4-carbon compounds. Succinic acid can also be used for producing biodegradable polymers.

SUMMARY

The present invention fulfills these needs and discloses methods of producing C4 dicarboxylic acids by fermentation.

In one embodiment, an isolated or recombinant polynucleotide comprises a sequence selected from the group consisting of: a polynucleotide sequence that encodes a polypeptide comprising SEQ ID NO: 2; a nucleotide sequence which is fully complementary to the polynucleotide sequence that encodes the polypeptide comprising SEQ ID NO: 2; and a sequence that hybridizes to the nucleotide sequence which is fully complementary to the polynucleotide sequence of that encodes the polypeptide comprising SEQ ID NO: 2 under stringent conditions comprising 0.2×SSC at 65° C.

In another embodiment, a vector comprises a promoter and means for expressing a pyruvate carboxylase protein of *Rhizopus* origin.

In yet an additional embodiment, a method of producing a C4 dicarboxylic acid, comprises growing a recombinant cell transformed with a sequence selected from the group consisting of: SEQ ID NO: 1; a full length complement of SEQ ID NO: 1; a sequence having at least 95% sequence identity to SEQ ID NO: 1 and encoding a polypeptide having pyruvate carboxylase activity; a sequence that encodes a polypeptide comprising the amino acid sequence of SEQ ID NO: 2; and a sequence of a polynucleotide that encodes a polypeptide having pyruvate carboxylase activity, wherein the polynucleotide hybridizes to the full-length complement of the polynucleotide of SEQ ID NO: 1 under stringent conditions comprising 0.2×SSC at 65° C. in a culture medium; and recovering the C4 dicarboxylic acid from the culture medium.

BRIEF DESCRIPTION OF THE DRAWINGS

FIGS. 3A-C show a cDNA sequence (SEQ ID NO:1) (FIGS. 3A-B) and a protein sequence (SEQ ID NO:2) (FIG. 3C) of *R. oryzae* 1526 pyruvate carboxylase. The open reading frame encodes a protein of 1179 amino acids.

DETAILED DESCRIPTION OF THE INVENTION

Figure 1:
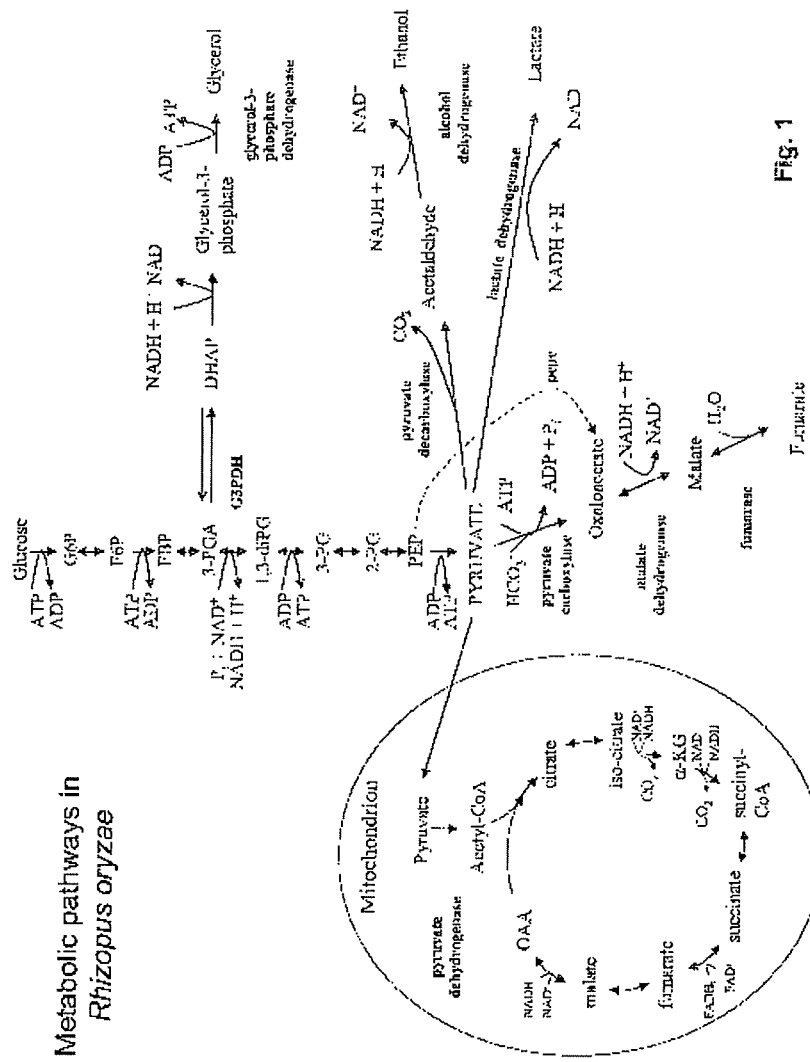
FIG. 1 is a diagram of the common metabolic pathways in *R. oryzae*.

In one embodiment, a recombinant host cell transformed with pyruvate carboxylase is fermented to produce a C4 dicarboxylic acid. The pyruvate carboxylase may be from a *Rhizopus* origin. The recombinant host cell is any variety of a host cell that is amenable to genetic manipulation and capable of growth on a large scale.

As used herein, the term "host cell" includes any prokaryotic or eukaryotic cell where a desired nucleic acid sequence has been introduced into the cell. The metabolic processes and pathways of such a host cell are capable of maintaining, replicating, and/or expressing a vector containing a foreign gene or DNA molecule. There are a variety of suitable host cells, including but not limited to bacterial, fungal, insect, mammalian, and plant cells, that can be utilized in various ways (for example, as a carrier to maintain a plasmid comprising a desired sequence). Representative microbial host cells include, but are not limited to, fungal cells such as *Rhizopus* ssp., *Saccharomyces* ssp., *Streptomyces* ssp., *Pichia* ssp., *Aspergillus* ssp., and bacterial cells such as *Lactobacillus* ssp., *Escherichia* ssp., *Corynebacterium* ssp., *Brevibacterium* ssp., *Pseudomonas* ssp., *Proteus* ssp., *Enterobacter* ssp., *Citrobacter* ssp., *Erwinia* ssp., *Xanthomonas* ssp., *Flavobacterium* ssp., *Streptococcus* ssp., *Lactococcus* ssp., *Leuconostoc* ssp., and *Enterococcus* ssp. In certain embodiments, the host cell may be *Rhizopus oryzae*. In certain other embodiments, the host cell may be *Escherichia coli*.

In another embodiment, the host cell may be a yeast cell of a genus of *Saccharomyces, Zygosaccharomyces, Candida, Hansenula, Kluyveromyces, Debaromyces, Nadsonia, Lipomyces, Torulopsis, Kloeckera, Pichia, Schizosaccharomyces, Trigonopsis, Brettanomyces, Cryptococcus, Trichosporon, Aureobasidium, Lipomyces, Phaffia, Rhodotorula, Yarrowia*, or *Schwanniomyces*.

When the host cell is a fungal cell, the fungal cell may be of a genus of *Saccharomyces, Zygosaccharomyces, Yarrowia, Kluyveromyces, Aspergillus* or *Pichia*. The fungal cell may also be of a filamentous fungus origin.

The host cell may be a bacterial cell of a genus of *Lactobacillus, Escherichia, Corynebacterium, Brevibacterium, Pseudomonas, Proteus, Enterobacter, Citrobacter, Erwinia, Xanthomonas, Flavobacterium, Streptococcus, Lactococcus, Leuconostoc*, and *Enterococcus*.

As disclosed herein, nucleic acid and protein sequences that encode pyruvate carboxylase are provided. In addition, methods of producing lactic acid, glycerol, malic acid, succinic acid or fumaric acid using host cells having a vector comprising the sequences are disclosed.

It is to be understood that certain descriptions of the present invention have been simplified to illustrate only those elements that are relevant to a clear understanding of the present invention, while eliminating, for purposes of clarity, other elements. Those of ordinary skill in the art, upon considering the present description of the invention, will recognize that other elements may be desirable in order to implement the present invention. However, because such other elements may be readily ascertained by one of ordinary skill upon considering the present description of the invention, and are not necessary for a complete understanding of the present invention, a discussion of such elements may not be provided herein. As such, it is to be understood that the description set forth herein is merely exemplary and is not intended to limit the scope of the claims.

Other than in the examples herein, or unless otherwise expressly specified, all of the numerical ranges, amounts, values and percentages, such as those for amounts of materials, elemental contents, times and temperatures of reaction, ratios of amounts, and others, in the following portion of the specification and attached claims may be read as if prefaced by the word "about", even though the term "about" may not expressly appear with the value, amount, or range. Accordingly, unless indicated to the contrary, the numerical parameters set forth in the following specification and attached claims are approximations that may vary depending upon the desired properties sought to be obtained by the present invention. At the very least, and not as an attempt to limit the application of the doctrine of equivalents to the scope of the claims, each numerical parameter should at least be construed in light of the number of reported significant digits and by applying ordinary rounding techniques.

Notwithstanding that the numerical ranges and parameters setting forth the broad scope of the invention are approximations, the numerical values set forth in the specific examples are reported as precisely as possible. Any numerical value, however, may contain error(s) necessarily resulting from the standard deviation found in its underlying respective testing measurements. Furthermore, when numerical ranges are set forth herein, these ranges are inclusive of the recited range end points (end points may be used). When percentages by weight are used herein, the numerical values reported are relative to the total mass weight. Those of skill in the art recognize that percent mass weight and actual mass weight are interconvertable.

Also, it should be understood that any numerical range recited herein is intended to include all sub-ranges subsumed therein. For example, a range of "1 to 10" is intended to include all sub-ranges between (and including) the recited minimum value of 1 and the recited maximum value of 10, that is, having a minimum value equal to or greater than 1 and a maximum value of equal to or less than 10. The terms "one," "a," or "an" as used herein are intended to include "at least one" or "one or more," unless otherwise indicated.

All referenced patents, patent applications, publications, sequence listings, electronic copies of sequence listings, or other disclosure material are incorporated by reference in whole but only to the extent that the incorporated material does not conflict with existing definitions, statements, or other disclosure material set forth in this disclosure. As such, and to the extent necessary, the disclosure as explicitly set forth herein supersedes any conflicting material incorporated herein by reference. Any material, or portion thereof, that is said to be incorporated by reference herein, but which conflicts with existing definitions, statements, or other disclosure material set forth herein will only be incorporated to the extent that no conflict arises between that incorporated material and the existing disclosure material.

As used herein, the term "fumaric acid" includes fumaric acid in either the free acid or salt form. As used herein, the term "malic acid" includes malic acid in either the free acid or salt form. As used herein, the term "succinic acid" includes succinic acid in either the free acid or salt form.

As used herein, the term "gene" includes a segment of nucleic acid, DNA or RNA, which encodes and is capable of expressing a specific gene product. A gene often produces a protein or polypeptide as its gene product, but in its broader sense, a gene can produce any desired product, whether the product is a protein, polypeptide or nucleic acid. Functional or structural nucleic acid, such as, without limitation, rRNA, ribozymes, antisense RNA or interfering RNA (e.g., siRNA) also may be considered "gene products." A "gene" may also contain sequences containing regulatory elements, such as, without limitation, promoters, enhancers and terminators; such regulatory elements may be "operably linked," most typically in an appropriate proximity to each other. Such promoters operate in cis (attached to each other on the same nucleic acid molecule) to cause expression of "a gene product." The choice of gene constituents, such as the particular combination of regulatory elements and expressed sequence, will dictate the conditions of expression. For example, a constitutive promoter, such as the CMV (cytomegalovirus) promoter, coupled to an expressed sequence will cause constitutive expression of the expressed sequence when transferred into a suitable host cell. A promoter is considered constitutive if it functions to promote transcription of a gene under normal growth conditions. A constitutive promoter is not tissue specific or developmentally specific, has broad cross-species tropism, and typically does not vary substantially in its expression under normal growth conditions.

A "gene" can also include introns or other DNA sequences that can be spliced from the final RNA transcript. An expressed DNA sequence that encodes a protein or peptide ("protein encoding sequence") includes an open reading frame (ORF). The protein encoding sequence may comprise intervening introns. Further, the term "gene" includes expressed sequences as well as non-expressed sequences. All DNA sequences provided herein are understood to include complementary strands unless otherwise noted. Furthermore, RNA sequences can be prepared from DNA sequences by substituting uracil for thymine, and are included in the scope of this definition and the invention, along with RNA copies of the DNA sequences of the invention isolated from cells.

As used herein, the term "oligonucleotide" includes a nucleic acid of from about 7 to about 50 bases though they are more typically from about 15 to about 35 bases. Oligonucleotides are useful as probes or primers for use in hybridization or amplification assays such as Southern or Northern blots; molecular beacon; polymerase chain reaction (PCR); reverse transcriptive PCR (RT-PCR); quantitative RT-PCR (QRT-PCT), e.g., TAQMAN; isothermal amplification methods, such as NASBA (nucleic acid sequence-based amplification); and rolling circle amplification, including use of padlock probes. The oligonucleotides of the invention can be modified by the addition of peptides, labels (including fluorescent, quantum dot, or enzyme tags), and other chemical moieties and are understood to be included in the scope of this definition and the invention.

As used herein, in the context of the novel nucleotide sequences described herein, a nucleic acid is "specific to" a given sequence, such as the pyruvate carboxylase cDNA and genomic sequences provided, if it can hybridize specifically to a given sequence under stringent conditions, such as, without limitation, 0.2×SSC at 65° C. or in a PCR reaction under typical reaction (annealing) temperatures. Typically, one sequence is "specific" to a reference sequence if the nucleic acid has 90 to 100% homology (sequence identity) to the reference sequence.

The following terms are used to describe the sequence relationships between two or more nucleic acids or polynucleotides: (a) "reference sequence", (b) "comparison window", (c) "sequence identity", (d) "percentage of sequence identity", and (e) "substantial identity". As used herein, "reference sequence" is a defined sequence used as a basis for sequence comparison. A reference sequence may be a subset or the entirety of a specified sequence; for example, as a segment of a full-length cDNA or gene sequence, or the complete cDNA or gene sequence. As used herein, "comparison window" makes reference to a contiguous and specified segment of a polynucleotide sequence, wherein the polynucleotide sequence in the comparison window may comprise additions or deletions (i.e., gaps) compared to the reference sequence (which does not comprise additions or deletions) for optimal alignment of the two sequences. Generally, the comparison window is at least 20 contiguous nucleotides in length, and optionally can be 30, 40, 50, 100, or longer. Those of ordinary skill in the art understand that to avoid a high similarity to a reference sequence due to inclusion of gaps in the polynucleotide sequence a gap penalty is typically introduced and is subtracted from the number of matches. Methods of alignment of sequences for comparison are well known. Thus, the determination of percent sequence identity between any two sequences can be accomplished using a mathematical algorithm. Non-limiting examples of such mathematical algorithms are the algorithm of Myers and Miller (1988) CABIOS 4:11-17; the local alignment algorithm of Smith et al. (1981) Adv. Appl. Math. 2:482; the global alignment algorithm of Needleman and Wunsch (1970) J. Mol. Biol. 48:443-453; the search-for-local alignment method of Pearson and Lipman (1988) Proc. Natl. Acad. Sci. 85:2444-2448; the algorithm of Karlin and Altschul (1990) Proc. Natl. Acad. Sci. USA 872264, as modified in Karlin and Altschul (1993) Proc. Natl. Acad. Sci. USA 90:5873-5877.

Computer implementations of these mathematical algorithms can be utilized for comparison of sequences to determine sequence identity. Such implementations include, but are not limited to: CLUSTAL in the PC/Gene program (available from Intelligenetics, Mountain View, Calif.); the ALIGN program (Version 2.0) and GAP, BESTFIT, BLAST, FASTA, and TFASTA in the GCG Wisconsin Genetics Software Package, Version 10 (available from Accelrys Inc., 9685 Scranton Road, San Diego, Calif., USA).

As used herein, "sequence identity" or "identity" in the context of two nucleic acid or polypeptide sequences makes reference to the residues in the two sequences that are the same when aligned for maximum correspondence over a specified comparison window. When percentage of sequence identity is used in reference to proteins, it is recognized that residue positions which are not identical often differ by conservative amino acid substitutions, where amino acid residues are substituted for other amino acid residues with similar chemical properties (e.g., charge or hydrophobicity) and therefore do not change the functional properties of the molecule. When sequences differ in conservative substitutions, the percent sequence identity may be adjusted upwards to correct for the conservative nature of the substitution. Sequences that differ by such conservative substitutions are said to have "sequence similarity" or "similarity." Means for making this adjustment are well known to those of skill in the art. Typically this involves scoring a conservative substitution as a partial rather than a full mismatch, thereby increasing the percentage sequence identity. Thus, for example, where an identical amino acid is given a score of 1 and a non-conservative substitution is given a score of zero, a conservative substitution is given a score between zero and 1. The scoring of conservative substitutions is calculated, e.g., as implemented in the program PC/GENE (Intelligenetics, Mountain View, Calif.).

As used herein, "percentage of sequence identity" means the value determined by comparing two optimally aligned sequences over a comparison window, wherein the portion of the polynucleotide sequence in the comparison window may comprise additions or deletions (i.e., gaps) as compared to the reference sequence (which does not comprise additions or deletions) for optimal alignment of the two sequences. The percentage is calculated by determining the number of positions at which the identical nucleic acid base or amino acid residue occurs in both sequences to yield the number of matched positions, dividing the number of matched positions by the total number of positions in the window of comparison, and multiplying the result by 100 to yield the percentage of sequence identity.

The term "substantial identity" of polynucleotide sequences means that a polynucleotide comprises a sequence that has at least 70% sequence identity, at least 80%, at least 90%, and at least 95%, compared to a reference sequence using one of the alignment programs described using standard parameters.

As used herein, a "primer" or "probe" for detecting a specific nucleic acid species includes any primer, primer set, and/or probe that can be utilized to detect and/or quantify the specific nucleic acid species. A "nucleic acid species" can be a single nucleic acid species, corresponding to a single gene, or can be nucleic acids that are detected by a single common primer and/or probe combination.

As used herein, the term "polynucleotide" includes any single-stranded sequence of nucleotide, connected by phosphodiester linkages, or any double-stranded sequences comprising two such complementary single-stranded sequences held together by hydrogen bonds. Unless otherwise indicated, each polynucleotide sequence set forth herein is presented as a sequence of deoxyribonucleotides (abbreviated A, G, C and T). The term "polynucleotide" encompasses DNA molecules or polynucleotide, sequences of deoxyribonucleotides, and RNA molecules or polyribonucleotides and combinations thereof.

As used herein, the term "promoter" includes a DNA sequence within a larger DNA sequence that provides or defines a site to which RNA polymerase can bind and initiate transcription. The promoters described herein can be used to over-express or up-regulate, for example, and without limitation, genes encoding enzymes that increase carbon flux to malic acid, fumaric acid, succinic acid and/or other desired metabolites during changes in fermentation conditions.

An "equivalent" of a given reference nucleotide sequence or element contained therein includes a nucleotide sequence containing, as compared to the reference nucleotide sequence, all elements of that reference nucleotide sequence, such that the characteristic function of that reference nucleic acid or peptide is retained. Those of skill in the art understand that a functional protein may be encoded by equivalent DNA sequences due to degeneracy in the genetic code. For example, one codon may be substituted for another, yet encode the same amino acid, such as, for example and without limitation, in reference to the Ala codon, the substitution of GCC or GCG for GCA. In the case of proteins, a sequence can contain amino acids that represent conservative amino acid substitutions, including but not limited to, the conservative substitution groups: Ser and Thr; Leu, Ile and Val; Glu and Asp; and Gln and Asn. A sequence as claimed herein thus includes the referenced sequence as well as its equivalents due to degeneracy in the genetic code. Conservative substitutions also can be determined by other methods, such as, without limitation, those used by the BLAST (Basic Local Alignment Search Tool) algorithm, the BLOSUM Substitution Scoring Matrix, and the BLOSUM 62 matrix (see also, for example, Altschul et al., *Methods in Enzymology* 266:460-479 (1996)). Importantly, "equivalents" and "conserved equivalents" of a reference nucleic acid or peptide/protein substantially retain or enhance the function of the reference nucleic acid or peptide/protein.

As used herein, the term "vector" includes a means for introducing a foreign nucleotide sequence into a cell, including without limitation, a plasmid or virus. Such vectors can operate under the control of a host cell's gene expression machinery. A vector contains sequences that facilitate replication and/or maintenance of a segment of foreign nucleic acid in the host cell. Generally, the vector is introduced into a host cell for replication and/or expression of the segment of foreign DNA or for delivery of the foreign DNA into the host genome. A typical plasmid vector contains: (i) an origin of replication, so that the vector can be maintained and/or replicated in a host cell; (ii) a selectable marker, such as an antibiotic resistance gene to facilitate propagation of the plasmid; and (iii) a polylinker site containing several different restriction endonuclease recognition and cut sites to facilitate cloning of a foreign DNA sequence.

RNA interference (RNAi) is a powerful and robust method for disrupting gene expression. It is based on a highly conserved gene silencing method that uses double-stranded RNA (dsRNA) or single-stranded RNA (ssRNA, see, e.g., Martinez J, et al., *Cell* 110(5):563-74 (2002)) as a signal to trigger the degradation of homologous cellular RNA. The mediators of the sequence-specific degradation are 21- to 23-nucleotide (nt) dsRNA small interfering RNAs (siRNA). Selection of appropriate siRNA sequences and preparation of the siRNA are discussed in detail in Elbashir, S. M. et al., *Methods* 26: 199-213 (2002) and in U.S. Patent Application Nos. 2002/0173478, 2002/0182223, 2002/0183276, 2002/0160393 and 2002/0162126.

Xia et al. describes construction of suitable plasmid containing a gene for expression of an siRNA. That reference also describes recombinant viral vectors and delivery systems The reference describes appropriate expression of an siRNA hairpin which down-regulation of the expression of a target β-glucuronidase gene in mouse brain and liver, thereby providing proof of concept of the usefulness of siRNA technology as a gene therapy for human diseases (Xia et al., *Nature Biotechnology*, 20:1006-1010 (2002)). See also, for example, U.S. Patent Application Nos. 2004/0241854 and 2004/0053876. Vectors for siRNA production are widely available from commercial sources, such as, without limitation, Ambion, Inc. of Austin Tex., Invivogen of San Diego, Calif., and GenScript Corporation of Piscataway, N.J. Vectors containing appropriate promoters, such as Pol III promoters, include for example and without limitation, H1 and U6 promoters and have proven especially useful in producing sufficient quantities of siRNA. A typical siRNA "gene" would therefore comprise an appropriate promoter operably linked to a sequence encoding an siRNA. Ambion's Technical Bulletin #506 ("siRNA Design Guidelines") provides non-limiting examples of siRNA design considerations. Computer software for generating suitable siRNA sequences from, for example and without limitation, a cDNA or ORF sequence also is commercially available.

Using well-established methods for determining effective siRNA sequences, siRNA sequences can be made to silence *R. oryzae* pyruvate dehydrogenase, pyruvate carboxylase and pyruvate decarboxylase. One non-limiting example of an siRNA sequence designed to silence the pyruvate dehydrogenase sequence from *R. oryzae* (FIG. 4) is: sense 5'-CAGACGAUGACCUUCCUUA (SEQ ID NO:3); antisense 5'-UAAGGAAGGUCAUCGUCUG (SEQ ID NO:4).

One non-limiting example of an siRNA sequence designed to silence pyruvate decarboxylase from *Rhizopus oryzae* (GenBank Accession Nos. AF282846 and AF282847) is: sense: 5'-CUUUGAUGUGUUCUUCAAC (SEQ ID NO:5); antisense 5'-GUUGAAGAACACAUCAAAG (SEQ ID NO:6).

One non-limiting example of an siRNA sequence designed to silence pyruvate carboxylase from *Rhizopus oryzae* is: sense 5'-UUGGCCACUCGUGUGAG (SEQ ID NO: 7); antisense 5'-CUCACACGAGUGGCCAA (SEQ ID NO: 8).

In one example, the sense/antisense pairs disclosed herein may be expressed under the control of the $P_{TEF}$ promoter or rRNA cluster promoter in a vector construct, such as for example and without limitation in pPYR225b containing the pyrG gene for selection.

Along with RNAi, antisense RNA is another method of interference with gene function. In antisense technology, RNA complementary to portions of mRNA is introduced into a cell, thereby down-regulating production of the protein product of the mRNA. Unlike RNAi technology, antisense does not completely silence the target gene in most cases. Production of useful antisense constructs and reagents are well within the abilities of those of ordinary skill in the art.

In one embodiment, a method for producing a C4 dicarboxylic acid comprises: growing a recombinant host cell transformed with a sequence selected from the group consisting of: SEQ ID NO: 1; a full length complement of SEQ ID NO: 1; a sequence having at least 95% sequence identity to SEQ ID NO: 1; and encoding a polypeptide having pyruvate carboxylase activity; a sequence that encodes a polypeptide comprising the amino acid sequence of SEQ ID NO: 2; and a sequence of a polynucleotide that encodes a polypeptide having pyruvate carboxylase activity, wherein the polynucleotide hybridizes to the full-length complement of the polynucleotide of SEQ ID NO: 1 under stringent conditions comprising 0.2×SSC at 65° C. in a culture medium; and recovering the C4 dicarboxylic acid from the culture medium. The C4 dicarboxylic acid may be selected from the group consisting of fumaric acid, succinic acid, or malic acid. In another embodiment, the C4 dicarboxylic acid is malic acid or succinic acid.

In one embodiment, a sequence having at least 95% sequence identity to SEQ ID NO: 1 is the pyruvate carboxylase gene disclosed in U.S. Pat. No. 7,435,168.

In another embodiment, a polynucleotide sequence that encodes a pyruvate carboxylase protein comprising SEQ ID NO: 2 is disclosed. In certain other embodiments, a nucleotide sequence which is fully complementary to the polynucleotide sequence that encodes the protein comprising SEQ ID NO: 2 may be disclosed. In other embodiments, a sequence that hybridizes to the nucleotide sequence which is fully complementary to the polynucleotide sequence of that encodes the protein comprising SEQ ID NO: 2 under stringent conditions comprising 0.2×SSC at 65° C. may be disclosed. For example, the sequences may encode, without limitation, pyruvate carboxylase (e.g., SEQ ID NO: 1).

In another embodiment, a vector comprises a promoter and means for expressing a pyruvate carboxylase protein of *Rhizopus* origin. In certain embodiments, the means for expressing a pyruvate carboxylase protein of *Rhizopus* origin is a polynucleotide that encodes an amino acid sequence of SEQ ID NO: 2, or is SEQ ID NO: 1.

In certain embodiments of the present disclosure, the polynucleotide may be isolated or recombinant. In certain other embodiments, the polynucleotide may further comprise a promoter operably linked to the polynucleotide sequence.

In certain embodiments of the present disclosure, a vector comprising the polynucleotide is disclosed. In certain other embodiments, the vector may comprise SEQ ID NO: 1. In other embodiments, the vector may include an open reading frame or coding sequence, with or without introns, for expressing pyruvate carboxylase. In specific embodiments, the pyruvate carboxylase may be of *Rhizopus oryzae* origin.

In certain embodiments, the vector may comprise a promoter and means for expressing a pyruvate carboxylase protein of *Rhizopus* origin. In certain other embodiments, the means for expressing a pyruvate carboxylase protein comprises SEQ ID NO: 1. In other embodiments, the means for expressing the pyruvate carboxylase protein comprises a polynucleotide sequence that encodes SEQ ID NO: 2.

Nucleic acids can be introduced into host cells according to standard methodologies including electroporation, or any other transformation or nucleic acid transfer method known in the art. For example, *R. oryzae* can be transfected by electroporation. *R. oryzae* cells can be permanently transformed by insertion of a gene of interest into the cell by electroporation, so long as the introduced DNA integrates into the host cell genome. This is accomplished, without any intention to be bound by this theory, by homologous recombination of the introduced DNA with the genomic DNA via single or double crossover, or is randomly integrated. The efficiency of transformation is increased when the introduced DNA is linearized and contains non-complementary ends, as is the case when a DNA fragment containing a gene is excised from a plasmid using two different restriction endonucleases which yield non-complementary ends. In such instances, the sequence can be purified from the plasmid backbone prior to transfection. Circularized DNA tends to concatamerize in *R. oryzae*, yielding large, circular extrachromosomal elements, which are eventually lost from the host cell during successive passage of the transfected cell line. Linearized DNA having complementary ends can also re-circularize and concatamerize (not necessarily in that order) and be lost in the same manner as an extrachromosomal element during successive passage of the transfected host cell line.

Host cells may be cultured under any conditions, such as those known in the art. As stated previously, fermentation conditions can affect the flux of carbon in an organism. For example, strong aeration shifts the flux of carbon to production of acetic acid and acetoin, and away from lactic acid production in lactic acid-producing bacteria. Fermentation conditions include, without limitation: the level of aeration, pH, and oxygen saturation level of the medium, as well as the amount of carbon and other growth factors available in the medium. The carbon source can be, for example and without limitation, various sugar alcohols, polyols, aldol sugars or keto sugars, including but not limited to arabinose, cellobiose, fructose, glucose, glycerol, inositol, lactose, maltose, mannitol, mannose, rhamnose, raffinose, sorbitol, sorbose, sucrose, trehalose, pyruvate, succinate or methylamine or other substrates which may be determined by one skilled in the art. As described herein, many organisms will thrive on common growth media. For example and without limitation, *R. oryzae* can be grown in LB (Luria-Bertani) Broth.

In a further example, antisense or RNAi technologies may be used alone, or in combination with increased gene expression of pyruvate carboxylase to further divert carbon from one metabolic pathway to another. It is noted that under some conditions, complete gene silencing may prevent sufficient cell culture growth unless a specific metabolite is provided in the culture medium (auxotroph). As used herein, the term "auxotroph" includes an organism that requires a specific growth factor (for example, an amino acid or sugar) for its growth.

Thus, production of a bradytroph may be optimized in many instances with antisense technology or RNAi technology. As used herein, the term "bradytroph" includes an organism that does not necessarily require a specific growth factor for its growth, but which produces a certain growth factor in lower amounts than a wild-type (w.t.) organism.

In certain embodiments, a cell co-transfected with genes for overexpressing pyruvate carboxylase and for down-regulating other known genes is disclosed. In one embodiment, the overexpression of pyruvate carboxylase catalyzes the conversion of pyruvate to oxaloacetate, which is a precursor of malate, fumarate and succinate. Thus, the overexpression of pyruvate carboxylase converts pyruvate to oxaloacetate. In another embodiment, a gene encoding malate dehydrogenase can be overexpressed to convert oxaloacetate to malate. In another embodiment, a gene encoding fumarase can be overexpressed to convert malate to fumarate. In yet another embodiment, a gene encoding fumarate reductase can be overexpressed to convert fumarate to succinate.

In certain embodiments of the present disclosure, methods of producing lactic acid, glycerol, malic acid, fumaric acid or succinic acid are disclosed. In certain other embodiments, the method may comprise growing a cell having a vector in a culture medium wherein the vector comprises a promoter and a means for expressing SEQ ID NO: 2 that is operably linked to the promoter. In other embodiments, the method may further comprise recovering at least one of the lactic acid, the glycerol, the fumaric acid, the malic acid or the succinic acid from the culture medium.

In another embodiment, the present disclosure provides an isolated or recombinant polynucleotide comprising a sequence selected from the group consisting of: a polynucleotide sequence that encodes a protein comprising SEQ ID NO: 2; a nucleotide sequence which is fully complementary to the polynucleotide sequence that encodes the protein comprising SEQ ID NO: 2; and a sequence that hybridizes to the nucleotide sequence which is fully complementary to the polynucleotide sequence of that encodes the protein comprising SEQ ID NO: 2 under stringent conditions comprising 0.2×SSC at 65° C.

In another embodiment, the present disclosure provides a vector comprising a promoter and means for expressing a pyruvate carboxylase protein of Rhizopus origin.

In another embodiment, the present disclosure provides a method of producing lactic acid, glycerol, malic acid, fumaric acid or succinic acid, comprising: growing a cell having a vector in a culture medium, the vector comprising: a promoter; and a means for expressing SEQ ID NO:2 that is operably linked to the promoter.

The various embodiments of the present disclosure may be better understood when read in conjunction with the following Examples.

EXAMPLES

The following examples illustrate various non-limiting embodiments of the nucleic acids and protein sequences encoding pyruvate carboxylase of Rhizopus of the present disclosure and are not restrictive of the invention as otherwise described herein.

Example 1

Rhizopus oryzae Pyruvate Carboxylase

The isolation and characterization of Rhizopus oryzae genomic and cDNA is described herein. Both the nucleic acid molecule and the encoded pyruvate carboxylase protein are provided. The properties of this enzyme and potential application for C4 dicarboxylic acid production are discussed.

As part of an effort to characterize the genes encoding the enzymes in the pathway leading to the synthesis of lactic acid, C4 dicarboxylic acids, ethanol and glycerol during fermentation, a pyruvate carboxylase gene was isolated from R. oryzae and the relatedness of its deduced protein to other known orthologs was studied. Two degenerate oligonucleotide primers were synthesized based on conserved regions pyruvate carboxylase-related amino acid sequences of A. bisporus (GenBank Accession No.: AJ276430), A. terreus (GenBank Accession No.: AF097728), P. pastoris (GenBank Accession No.: Y11106), and S. pombe (GenBank Accession No.: D78170). Amplification by polymerase chain reaction (PCR) with R. oryzae genomic DNA as template yielded a product of the predicted size (648 bp). Additional PCR reactions using gene-specific and degenerate primers were used to isolate the pyruvate carboxylase gene and cDNA fragments from R. oryzae. The cDNA, genomic DNA, and encoded amino acid sequence of the protein, were described (SEQ ID NOS:1-2) (FIGS. 3A-C).

Rhizopus oryzae strain 1526 was maintained on YM agar plates (per liter: 3 g yeast extract, 3 g malt extract, 5 g peptone, 10 g dextrose, and 20 g agar). The fungus was grown in YML liquid media (per liter: 3 g yeast extract, 3 g malt extract, 5 g peptone, and 10 g dextrose) at room temperature with shaking (100 to 150 rpm) or YM agar plates at 30° C.

DNA and total RNA were extracted from frozen spores (−80° C.) of R. oryzae. Genomic DNA was isolated using the Omniprep™ purification system (Geno Technology, Inc., St. Louis, Mo.) or by a CTAB buffer (100 mM Tris-HCl, pH 7.5, 1% mixed alkyltri-methyl ammonium bromide (Sigma, St. Louis, Mo.), 0.7M NaCl, 10 mM EDTA 1% β-mercaptoethanol (v/v)) plus 0.03% proteinase K. The frozen spores were ground by mortar and pestle and extracted in the CTAB buffer followed by incubation at 65° C. for 30 min. One volume of chloroform/isoamyl alcohol (24:1) was added, gently mixed for 5 min., and centrifuged at 3,000 rpm for 20 min. The supernatant was removed and a ⅔ volume of 2-propanol was added and recentrifuged as above. The precipitated DNA was rinsed with 75% ethanol and suspended in 0.5 ml sterile water. Contaminating RNA was removed by addition of 5 µl of 10 mg/ml RNAse A and incubated at 37° C. for about 30 min.

Total RNA was isolated using RNAqueous™ Kit (Ambion, Inc., Austin, Tex.) and mRNA was purified from the total RNA using the PolyATtract™ mRNA Isolation Systems (Promega Corporation, Madison, Wis.). The methods used for DNA and RNA electrophoresis have been described elsewhere (Sambrook, J., Fritsch, E. F., and Maniatis, T., in Molecular Cloning: A Laboratory Manual. Cold Spring Harbor Laboratory Press, NY, Vol. 1, 2, 3 (1989)).

PCR was performed in a GeneAmp PCR System 9700™ (Applied Biosystems, Foster City, Calif.) using Taq DNA polymerase (Life Technologies, Gaithersburg, Md.) and two degenerate primers based on conserved amino acid sequences of pyruvate carboxylase homologs from Aspergillus agricarus, A. terreus, Pichia pastoris, and Schizosaccharomyces pombe. Forward primer 5' CARAGRAGRCAYCARAARGT 3' (SEQ ID NO: 9) is based on the amino acid sequence "QRRHQKV," and reverse primer 5' TCRTCDATRAANGT-NGTCCA 3' (SEQ ID NO:10) is based on the amino acid sequence "WTTFIDD" (where Y=T or C; R=G or A; D=A, G or T; N=A, T, G, or C) (SEQ ID NO:11). The degenerate primers were used in Touchdown PCR (Don, R. H., et al., Nucleic Acids Res. 19:4008 (1991)) to amplify a 648-bp fragment from R. oryzae genomic DNA. Touchdown PCR was performed under the following conditions: initial denaturation at 94° C. for 3 min; 38 cycles of denaturation, 94° C. for 30 sec; annealing for 30 sec; and polymerization at 72° C. for 2 min. The annealing temperature ranged from 55° C. to 45° C. with a decrease of 1° C. every three cycles. This was followed by 14 cycles of denaturation at 94° C. for 1 min; annealing at 45° C. for 30 sec.; and polymerization at 72° C. for 2 min. The PCR product was cloned into pGEM T-easy™ vector (Promega, Madison, Wis.). Additional PCR products were isolated using pyruvate carboxylase (PYC) gene-specific primers, genomic DNA or cDNA and other degenerate primers.

The 5' end of the pyruvate carboxylase (PYC) cDNA was determined using the GeneRacer™ kit, following the instructions of the manufacturer (Invitrogen Corporation, Carlsbad, Calif.). A PYC-specific oligonucleotide of sequence 5'-CCAATACGACCGAGTTGATAGGATTCAT-3' (SEQ ID NO:12) was used to prime first-strand cDNA synthesis, which was then amplified by PCR using a nested primer of the sequence 5'-GCATAGATAATGTATCTTCATGA-3' (SEQ ID NO:13).

Automated fluorescence DNA sequencing was done at the W.M. Keck Center for Comparative and Functional Genomics Facility, University of Illinois at Urbana-Champaign. Sequence data were analyzed with DNASTAR™ software (DNASTAR, Inc., Madison, Wis.).

Figure 2:
FIG. 2 shows conserved domains among *R. oryzae*, *S. cerevisiae*, *A. niger*, *A. terreus*, *P. pastoris*, and *S. pombe* pyruvate carboxylase proteins. The two ATP binding domains and the biotin binding domains are 100% conserved, while the pyruvate binding domain is 89% conserved among these fungal proteins.
Figure 4:
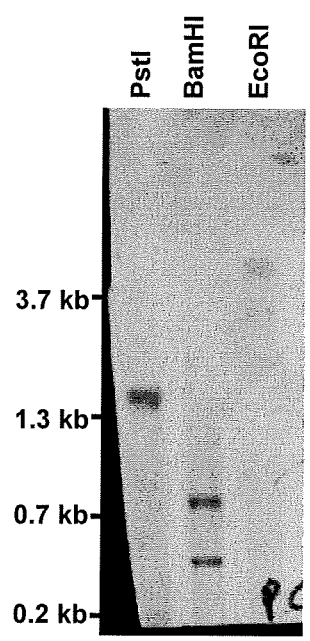
FIG. 4 shows a Southern blot of total genomic DNA from *R. oryzae* digested with restriction enzymes PstI, BamHI, or EcoRI showing relative copy numbers of the pyruvate carboxylase (pyrC) containing plasmid.

The open reading frame of the product of PYC, PYCp, is 1178 amino acids and has a molecular mass of 130 kD. PYCp has ~61 to 67% overall identity with *S. cerevisiae* (Morris, C. P., et al., *Biochem. Biophys. Res. Commun.* 145:390-396 (1987)); *Aspergillus niger* (Panneman, H., Ruijter, G. J. G., Van den Broeck, H. C. and Visser, J., unpublished); *A. terreus* (Li, Y. F., Chen, M. C., Lin, Y. H., Hsu, C. C. and Tsai, Y. C., unpublished); *P. pastoris* (Menendez, J., et al., *Yeast* 14:647-654 (1998)); and *S. pombe* (Saito, A., et al., unpublished) pyruvate carboxylase proteins. The similarity is very strong throughout the protein sequence (FIG. 2). The two ATP and biotin binding domains are 100% conserved, while the pyruvate binding domain is 89% conserved among these fungal proteins (FIG. 2), like its yeast homolog (Lim, F., et al., *Arch. Biochem. Biophys.* 258:259-264 (1987)). The PSORT program (Nakai, K., et al., *Genomics* 14:897-911 (1992)) strongly predicts the subcellular localization of *R. oryzae* pyruvate carboxylase to the cytoplasm. The computed probability of PYCp having a cytoplasmic localization is 78%. Hybridization of a PYC probe to a blot of *R. oryzae* genomic DNA digested with different restriction enzymes (PstI, BamHI, or EcoRI) resulted in a single band in one case and multiple bands in the others. Preliminary data indicates that there may be a single copy of this pyruvate carboxylase gene in *R. oryzae* (FIG. 4).

The production of fumaric acid by *R. oryzae* has been shown to result from a cytosolic pathway during which pyruvate is converted to oxaloacetate by pyruvate carboxylase (Osmani and Scrutton, *Ann NY Acad Sci* 447: 56-71 (1985)). Therefore, this gene expression can be enhanced by introducing multiple copies or expressing it from a strong promoter to increase production of a C4 dicarboxylic acid. Moreover, the disruption of this gene can also lead to the reduction of C4 dicarboxylic acid produced during lactic acid production by *R. oryzae*.

Example 2

Cloning of Pyruvate Carboxylase from *Rhizopus oryzae* NRRL Strain 1526

Mycelia were harvested 48 hours after inoculation into fumaric acid production media. Total RNA was isolated from the *Rhizopus oryzae* NRRL strain 1526 using an RNAqueous™ Kit as set forth in Example 1. The total RNA was used to generate cDNA using a GeneRacer™ kit as set forth in Example 1. One pyruvate carboxylase specific primer 5'-ATAACGATGCCTGCTGCACC-3' (SEQ ID NO: 14) and a GeneRacer™ kit 3' nested oligo dT primer 5' CGCTACGTAACGGCATGACAGTG 3' (SEQ ID NO: 15) were used to PCR amplify the pyrC cDNA. The pyrC-specific primer (SEQ ID No: 14) was designed from the pyrC genomic sequence cloned from the lactic acid producing *Rhizopus oryzae* NRRL 395. Once amplified, the putative pyrC cDNA was purified using Wizard® SV Gel and PCR clean-up system (Promega Corporation, Madison, Wis.). PCR-Script™ AMP Cloning kit (Stratagene, La Jolla, Calif.) was used to clone the amplicon into pPCRScript vector. The pyrC cDNA was subcloned into pPUC19, sequenced, and transformed into *E. coli* strain JCL1242 (a phosphoenolpyruvate carboxylase knockout) (Gokarn et al., *Appl. Microbiol. Biotech.*, 2001 (56): 188-195). The putative pyrC cDNA complemented the phosphoenolpyruvate (PEP) carboxylase deficiency to allow growth on glucose. After demonstrating growth on glucose by the PEP carboxylase deficient organism, the pyrC cDNA was subcloned (both by ligation dependent and ligation independent methods) into a variety of other vectors.

Example 3

Uracil auxotrophy has been successfully used as a selectable marker in the lactic acid producing *R. oryzae* strains (Skory, 2002). In order to test various constructs in the *R. oryzae* fumaric acid producer NRRL 1526, uracil auxotrophic strains were developed by NTG mutagenesis and subsequent screening on 5-fluoroorotic acid. Two strains were confirmed to be pyrG mutants via genetic complementation with the wild-type pyrG gene (GenBank Accession # AF497632) in the pyr225b vector (Skory, 2002). One of these strains, designated S3C6B was used for transformation.

Figure 5:
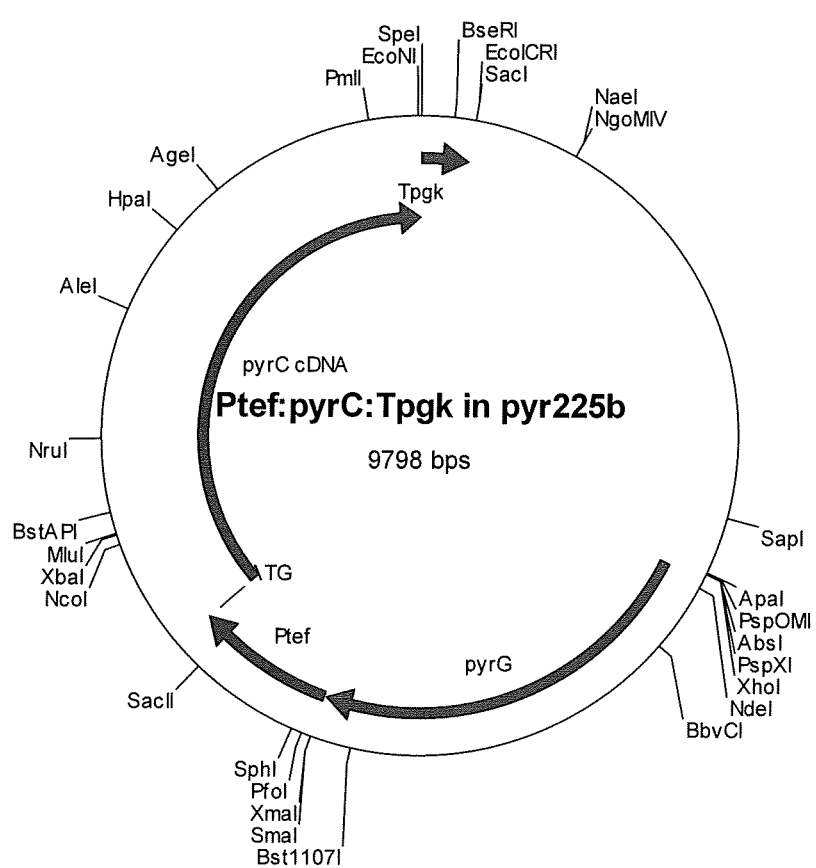
FIG. 5 is the Ptef:pyrC:Tpgk pyr225b plasmid map.

The pyrC cDNA from *R. oryzae* strain NRRL 1526 was fused to the *R. oryzae* TEF promoter ($P_{tef}$) by ligation independent cloning. The resulting fusion product and the phosphoglycerate kinase terminator ($T_{pgk}$) from *S. cerevisiae* were cloned into pyr225b, generating (FIG. 5) and confirmed by restriction enzyme digestion and PCR. The resulting construct, Ptef:pyrC:Tpgk pyr225b was transformed into the spores of the uracil auxotrophic strain of *R. oryzae* 1526 (S3C6B). Transformation was carried out by biolistic particle bombardment using 0.6 μm gold particles at a ⅛" gap distance in the PDS-1000 He System (Bio-Rad, Hercules, Calif.) outlined in (Skory, 2002). Five uracil prototrohpic putative transformants were recovered. The presence of Ptef:pyrC:Tpgk pyr225b DNA in the mycelium was confirmed by PCR using primers specific for pyrC and pyrG GGACTTCACACTGCATGGC (SEQ ID NO: 16) and GCTTGTCTACCAATTAGGTGCA (SEQ ID NO: 17), respectively.

Figure 6:
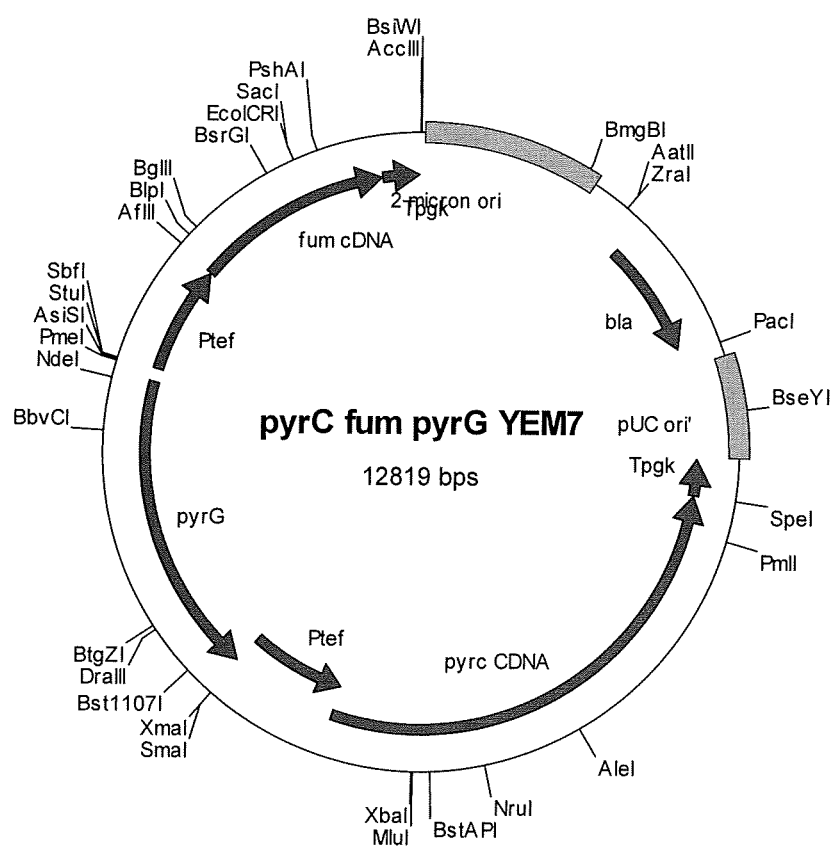
FIG. 6 is the pyrC fum pyrG YEM7 plasmid map.

The pyrC/pyrG cassette from Ptef:pyrC:Tpgk pyr225b was moved into the fungal episomal vector YEM7 containing a copy of the *R. oryzae* fumarase gene (cloned from *R. oryzae* NRRL 1526, GenBank accession # X78576) driven by the *R. oryzae* Ptef promoter to generate the plasmid pyrC fum pyrG YEM7 (FIG. 6). This plasmid was transformed as described in this Example. Five uracil prototrophic putative transformants were recovered and the presence of pyrC fum pyrG YEM7 DNA was confirmed by PCR using primers specific for pyrG and the Ptef:fum junction, CCGAGCCACAGATCAGGAAT (SEQ ID NO: 18) and GCAGAAGCTCGCAACATGGCTATGATGAA (SEQ ID NO: 19), respectively.

It should be understood that this invention is not limited to the embodiments disclosed in the summary, and it is intended to cover modifications that are within the spirit and scope of the invention, as defined by the claims.

What is claimed is:

1. An isolated or recombinant polynucleotide encoding a pyruvate carboxylase protein, the isolated or recombinant polynucleotide comprising a sequence selected from the group consisting of:
- a polynucleotide sequence that encodes a polypeptide comprising SEQ ID NO: 2;
- a nucleotide sequence which is fully complementary to the polynucleotide sequence that encodes the polypeptide comprising SEQ ID NO: 2; and
- a sequence that hybridizes to the nucleotide sequence which is fully complementary to the polynucleotide sequence that encodes the polypeptide comprising SEQ ID NO: 2 under stringent conditions comprising 0.2× SSC at 65° C.

2. The isolated or recombinant polynucleotide of claim 1, further comprising a promoter operably linked to the isolated or recombinant polynucleotide sequence.

3. The isolated or recombinant polynucleotide of claim 1, wherein the polynucleotide collide sequence that encodes the polypeptide comprising SEQ ID NO: 2 is SEQ NO: 1.

4. A vector comprising the isolated or recombinant polynucleotide of claim 1.

5. A vector comprising:
a promoter; and
an isolated or recombinant polynucleotide for expressing a pyruvate carboxylase protein of *Rhizopus* origin, the isolated or recombinant polynucleotide comprising a sequence selected from the group consisting of a polynucleotide sequence that encodes a polypeptide comprising SEQ ID NO: 2, a nucleotide sequence which is fully complementary to the polynucleotide sequence that encodes the polypeptide comprising SEQ ID NO: 2, and a sequence that hybridizes to the nucleotide sequence which is fully complementary to the polynucleotide sequence that encodes the polypeptide comprising SEQ ID NO: 2 under stringent conditions comprising 0.2×SSC at 65° C.

6. The vector of claim 5, wherein the isolated or recombinant polynucleotide comprises SEQ ID NO: 1.

7. The vector of claim 5, wherein the isolated or recombinant polynucleotide comprises the polynucleotide sequence that encodes SEQ ID NO: 2.

8. The vector of claim 5, wherein the pyruvate carboxylase is of a *Rhizopus oryzae* origin.

9. A host cell comprising the vector of claim 5.

10. The host cell of claim 9, wherein the host cell is of a genus selected from the group consisting of *Rhizopus, Saccharomyces, Streptomyces, Pichia, Aspergillus, Lactobacillus, Escherichia coli, Corynebacterium, Brevibacterium, Pseudomonas, Proteus, Enterobacter, Citrobacter, Erwinia, Xanthomonas, Flavobacterium, Streptococcus, Lactococcus, Leuconostoc,* and *Enterococcus*.

11. The host cell of claim 9, wherein the host cell is a filamentous fungus.

12. The host cell of claim 9, Wherein the host cell is of an *Aspergillus* genus.

13. A method of producing a C4 dicarboxylic acid, comprising:
growing a recombinant cell transformed with a sequence encoding a decarboxylase, the sequence being selected from the group consisting of: SEQ ID NO: 1; a full length complement of SEQ ID NO: 1; a sequence that encodes a polypeptide comprising the amino acid sequence of SEQ ID NO: 2; and a sequence of a polynucleotide that encodes a polypeptide having pyruvate carboxylase activity, wherein the polynucleotide hybridizes to the full-length complement of the polynucleotide of SEQ ID NO: 1 under stringent conditions comprising 0.2×SSC at 65° C. in a culture medium under conditions such that the recombinant cell produces the pyruvate decarboxylase; and
recovering the C4 dicarboxylic acid from the culture medium.

14. The method of claim 13, wherein the recombinant cell is of a genus selected from the group consisting of *Rhizopus, Saccharomyces, Streptomyces, Pichia, Aspergillus, Lactobacillus, Escherichia coli, Corynebacterium, Brevibacterium, Pseudomonas, Proteus, Enterobacter, Citrobacter, Erwinia, Xanthomonas, Flavobacterium, Streptococcus, Lactococcus, Leuconostoc,* and *Enterococcus*.

15. The method of claim 13, wherein the recombinant cell is a filamentous fungus.

16. The method of claim 15, wherein the filamentous fungus is *Aspergillus*.

17. The method of claim 13, wherein the recombinant cell is of a *Rhizopus* origin.

18. The method of claim 13, wherein the C4 dicarboxylic acid is selected from the group consisting of malic acid, fumaric acid and succinic acid.

19. The method of claim 13, wherein the C4 dicarboxylic acid is malic acid.

\* \* \* \* \*